United States Patent
Sater

(10) Patent No.: US 7,473,274 B2
(45) Date of Patent: Jan. 6, 2009

(54) CORONARY SINUS APPROACH FOR REPAIR OF MITRAL VALVE REGURGITATION

(75) Inventor: Ghaleb Sater, Acton, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 105 days.

(21) Appl. No.: 10/531,818

(22) PCT Filed: Nov. 11, 2004

(86) PCT No.: PCT/US2004/038005

§ 371 (c)(1),
(2), (4) Date: Jun. 1, 2006

(87) PCT Pub. No.: WO2005/046531

PCT Pub. Date: May 26, 2005

(65) Prior Publication Data

US 2006/0247763 A1    Nov. 2, 2006

Related U.S. Application Data

(60) Provisional application No. 60/519,115, filed on Nov. 12, 2003.

(51) Int. Cl.
A61F 2/24 (2006.01)
(52) U.S. Cl. ..................... 623/2.37; 623/2.11
(58) Field of Classification Search ............ 623/2.36, 623/2.37, 2.11
See application file for complete search history.

(56) References Cited

U.S. PATENT DOCUMENTS

| | | | | |
|---|---|---|---|---|
| 4,604,995 A * | 8/1986 | Stephens et al. | ............ | 606/61 |
| 5,059,193 A * | 10/1991 | Kuslich | ............ | 606/247 |
| 5,591,197 A * | 1/1997 | Orth et al. | ............ | 623/1.16 |
| 5,752,969 A * | 5/1998 | Cunci et al. | ............ | 606/167 |
| 6,245,101 B1 * | 6/2001 | Drasler et al. | ............ | 623/1.15 |
| 6,290,673 B1 * | 9/2001 | Shanley | ............ | 604/102.02 |
| 6,793,673 B2 * | 9/2004 | Kowalsky et al. | ............ | 623/2.36 |
| 2002/0183835 A1 * | 12/2002 | Taylor et al. | ............ | 623/2.11 |
| 2002/0183836 A1 | 12/2002 | Liddicoat et al. | | |
| 2002/0183837 A1 * | 12/2002 | Streeter et al. | ............ | 623/2.11 |
| 2002/0183838 A1 | 12/2002 | Liddicoat et al. | | |
| 2002/0183841 A1 | 12/2002 | Cohn et al. | | |
| 2003/0078654 A1 * | 4/2003 | Taylor et al. | ............ | 623/2.36 |
| 2003/0212453 A1 | 11/2003 | Mathis et al. | | |
| 2004/0249452 A1 * | 12/2004 | Adams et al. | ............ | 623/2.36 |

FOREIGN PATENT DOCUMENTS

| WO | WO 02/091908 | 11/2002 |
|---|---|---|
| WO | WO 02/096275 | 12/2002 |

* cited by examiner

*Primary Examiner*—Paul Prebilic

(57) ABSTRACT

A device, system and method for treating cardiac valve regurgitation. The device includes a compression member disposed on a tube and a sleeve rotatably disposed about the tube and the compression member. The sleeve includes a side port, and is rotatable to align the compression member with the side port to transform the compression member from a delivery configuration to a compression configuration. One method includes positioning the compression member adjacent a cardiac valve and rotating the sleeve to align the compression member with the side port to release the compression member from the delivery configuration to the compression configuration to apply a compressive force to the cardiac valve.

9 Claims, 7 Drawing Sheets

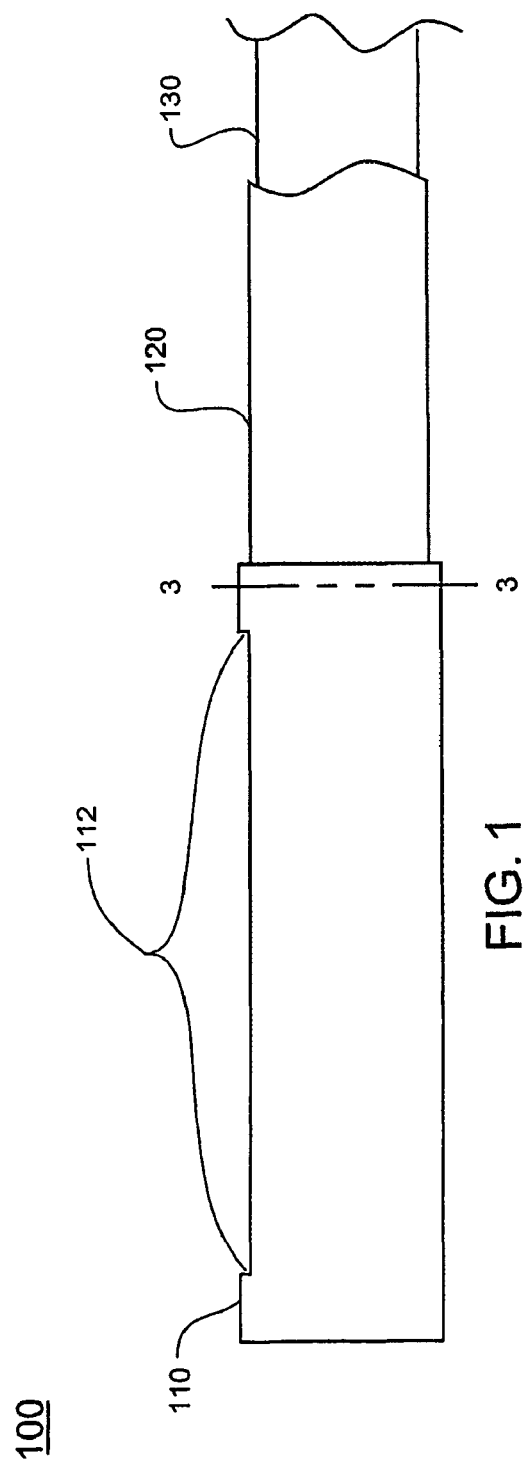
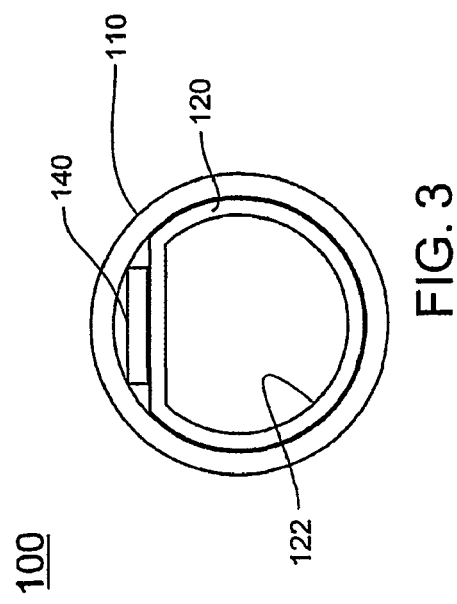

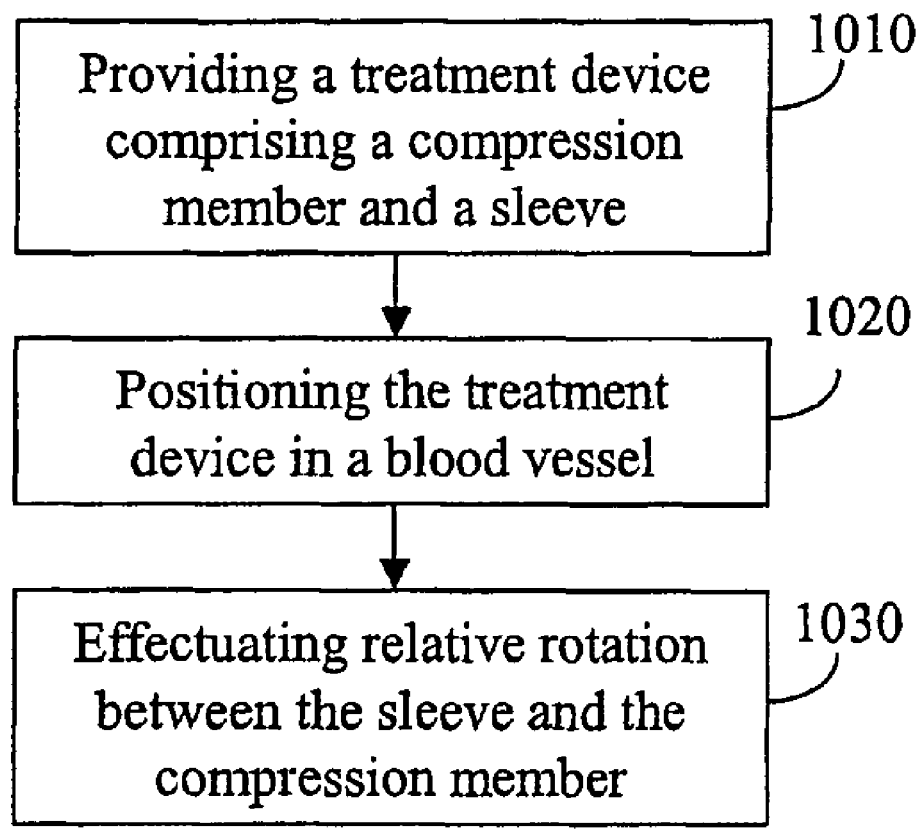

CORONARY SINUS APPROACH FOR REPAIR OF MITRAL VALVE REGURGITATION

TECHNICAL FIELD

The technical field of this disclosure is medical devices, particularly for treating mitral valve regurgitation.

BACKGROUND OF THE INVENTION

Valve insufficiency and regurgitation is a potentially grave health issue that can lead to cardiac dysfunction. Mitral valve insufficiency may comprise a valve that does not completely shut and affect the seal between the left ventricle and the left atrium. Historically, such a condition necessitated surgical intervention.

Surgical repair of mitral valve insufficiency historically involved the use of a sternotomy or a similar invasive procedure. After performing a sternotomy, the patient's heart would be stopped while the surgeon transected the chambers of the heart to gain access to the mitral valve. Upon attaining access to the mitral valve, the surgeon could then repair the valve by an annuloplasty, or suturing the valve. These procedures are complex, time consuming, and involve many risks attendant with open cardiac surgery. Complications may occur, and recovery time may be significant.

Catheter based valve replacement has been proposed as a way to avoid open-heart surgery. Such procedures involve excision of the native valve and replacement of the native valve with a prosthetic valve, or installation of a prosthetic valve over the native valve, or a device to repair the damaged valve. Previous proposed treatments involve the use of clips to bind the posterior and anterior leaflets of the mitral valve. To avoid cardiopulmonary bypass, the catheter based valve replacement is performed on a beating heart. Following excision of the native valve, no valve is present to preserve the pumping action of the heart while the permanent prosthetic valve is being implanted.

An additional consideration in both open-heart and catheter based valve replacement is the healing process after the prosthetic valve is implanted. After the surgical valve replacement procedure, scar tissue must form around the sewing cuff to secure the prosthetic valve in position. In current practice, multiple knotted sutures anchor the prosthetic valve in place until in-growth of scar tissue into the sewing cuff takes over the load bearing function. However, the placement of knotted sutures through a catheter can be very difficult and time consuming.

Artificial heart valves for temporary use are known in the art, but present certain problems. Some designs are complex, requiring alternating the inflation and deflation of balloons to alternately block and permit flow. Such designs require complex sensing and control systems. Other designs fail to provide access for tools that must reach the valve site for removal of the native valve and placement of the prosthetic valve. Yet other designs require elaborate supporting frames to hold the valve portion.

Alternative procedures to effect cardiac valve regurgitation involve the implantation of a device into the coronary sinus near the mitral valve. Some of these devices attempt to correct mitral valve regurgitation by placing a compressive force on the coronary sinus that then compresses at least a portion of the mitral valve annulus adjacent the coronary sinus. The resultant reduction in annulus radius brings the valve leaflets closer together to decrease the valve regurgitation. Still other devices that are implanted in the coronary sinus attempt to decrease valve regurgitation by straightening the radius of the coronary sinus. Straightening the coronary sinus results in a corresponding straightening of a portion of the mitral valve annulus adjacent the straightened coronary sinus. The intended result is to draw the valve leaflets closer together to decrease the valve regurgitation. One drawback to these implanted devices is that the size and shape of these devices often impede the flow of blood through the coronary sinus.

It would be desirable, therefore, to provide an apparatus and method for reducing cardiac valve regurgitation that overcomes these and other disadvantages.

SUMMARY OF THE INVENTION

One embodiment of the invention provides a device for treating cardiac valve regurgitation. The device comprises a tube having a lumen there through, a compression member carried on the tube and a sleeve disposed about the tube and compression member. The sleeve includes a side port and is rotatable about the tube to align the side port with the compression member to release the compression member into a compression configuration. As used herein, the term "compression" refers to the force applied by the inventive device to the annulus of a cardiac valve to effect a reduction in diameter or other transverse dimension of the valve.

A second embodiment of the invention provides a system for treating cardiac valve regurgitation. The system includes a delivery catheter, a treatment device and a release mechanism to releasably connect the delivery catheter to the treatment device. The treatment device comprises a compression member carried on a tube and a sleeve having a side port, wherein the sleeve is rotatable about the compression member and the tube.

Another embodiment of the invention provides a method for treating mitral valve regurgitation. The method includes providing a treatment device comprising a compression member disposed exteriorly on a tube and a sleeve rotatably disposed about the tube and the compression member. The treatment device is positioned in a blood vessel adjacent a cardiac valve. Relative rotation between the sleeve and the compression member aligns the compression member with a side port in the sleeve, thus deploying the compression member through the side port and into contact with the blood vessel. Deploying the compression member deforms the blood vessel and applies a compressive force to the cardiac valve The foregoing aspects and other attendant advantages of the present invention will become more readily appreciated by the detailed description taken in conjunction with the accompanying drawings, which are not drawn to scale. The detailed description and drawings are merely illustrative of the invention rather than limiting, the scope of the invention being defined by the appended claims and equivalents thereof.

BRIEF DESCRIPTION OF THE FIGURES

FIG. 1 illustrates a side view of an embodiment of a device prior to deployment in accordance with an aspect of the invention;

FIG. 3 illustrates a transverse cross section of the device illustrated in FIG. 1, taken along line 3-3;

FIG. 10 is a flowchart illustrating a method for treating cardiac valve regurgitation In accordance with one embodiment of the present invention;

DETAILED DESCRIPTION OF THE PRESENTLY PREFERRED EMBODIMENTS

FIGS. 1-4 illustrate one embodiment of a treatment device 100 for reducing valve regurgitation in accordance with the present invention. Throughout, the terms "distal" and "proximal" are used herein with reference to the treating clinician during deployment of the device; "Distal" indicates a portion distant from, or a direction away from the clinician and "proximal" indicates a portion near to, or a direction towards the clinician. Throughout the following description like elements will have like reference numbers as those of FIG. 1. Treatment device 100 is described below in reference to the mitral valve. Those with skill in the art will recognize that the teachings of the present invention may be applied to other valves, such as, for example, the tricuspid valve.

Figure 2:
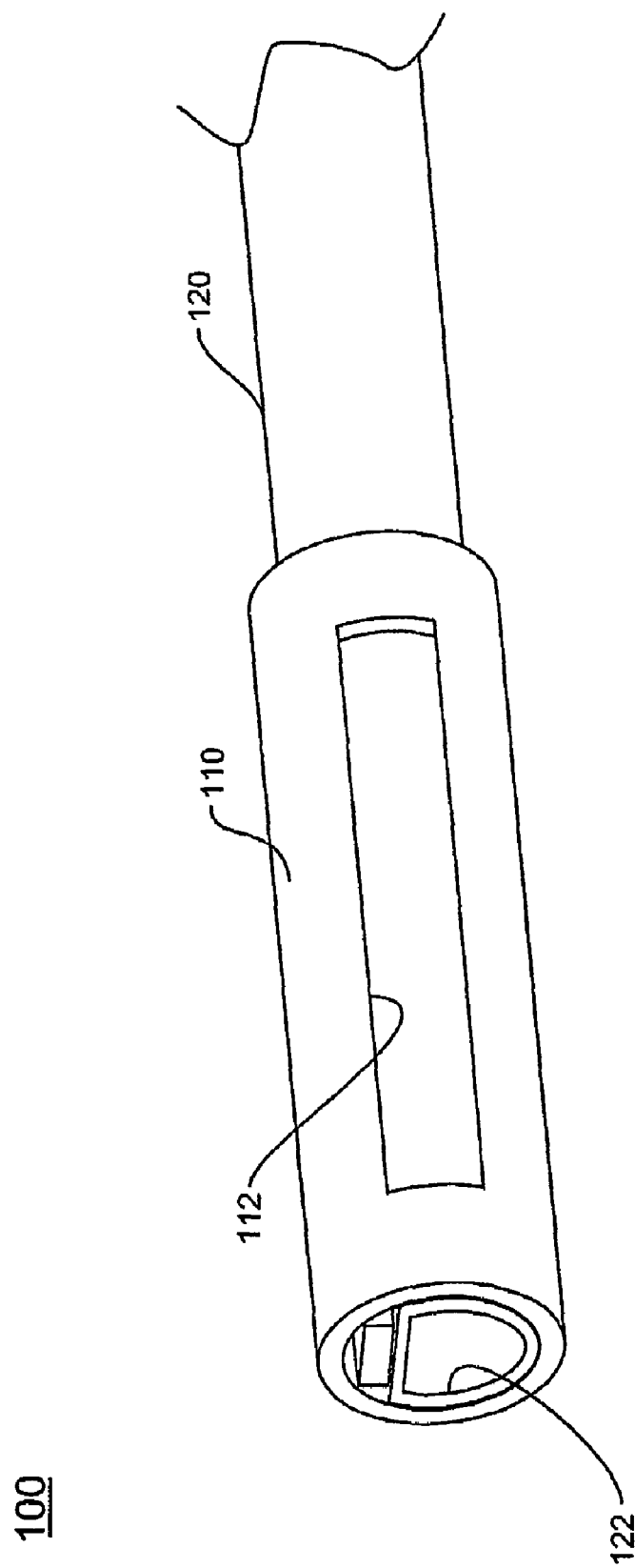
FIG. 2 illustrates a perspective view of the device illustrated in FIG. 1.

FIG. 1 is a side view of treatment device 100 and FIG. 2 is a perspective view of treatment device 100. Treatment device 100 comprises an elongated device including sleeve 110 and tube 120. Sleeve 110 includes side port 112 formed therein. Sleeve 110 is rotatably carried upon tube 120. Tube 120 includes central lumen 122 extending there through. Lumen 122 comprises a centrally located co-axial lumen that runs the entire length of tube 120 to thereby provide a substantially unimpeded flow of blood through the vessel into which it is implanted, e.g. the coronary sinus. Those with skill In the art will recognize that lumen 122 may not be co-axial with tube 120 though still provide a substantially unimpeded flow of blood. Sleeve 110 and tube 120 comprise materials that are sufficiently rigid to maintain their shape in response to axial and radial forces, while being sufficiently flexible to navigate the patient's vasculature as they travel to the coronary sinus. Tube 120 is carried upon catheter 130.

Figure 4:
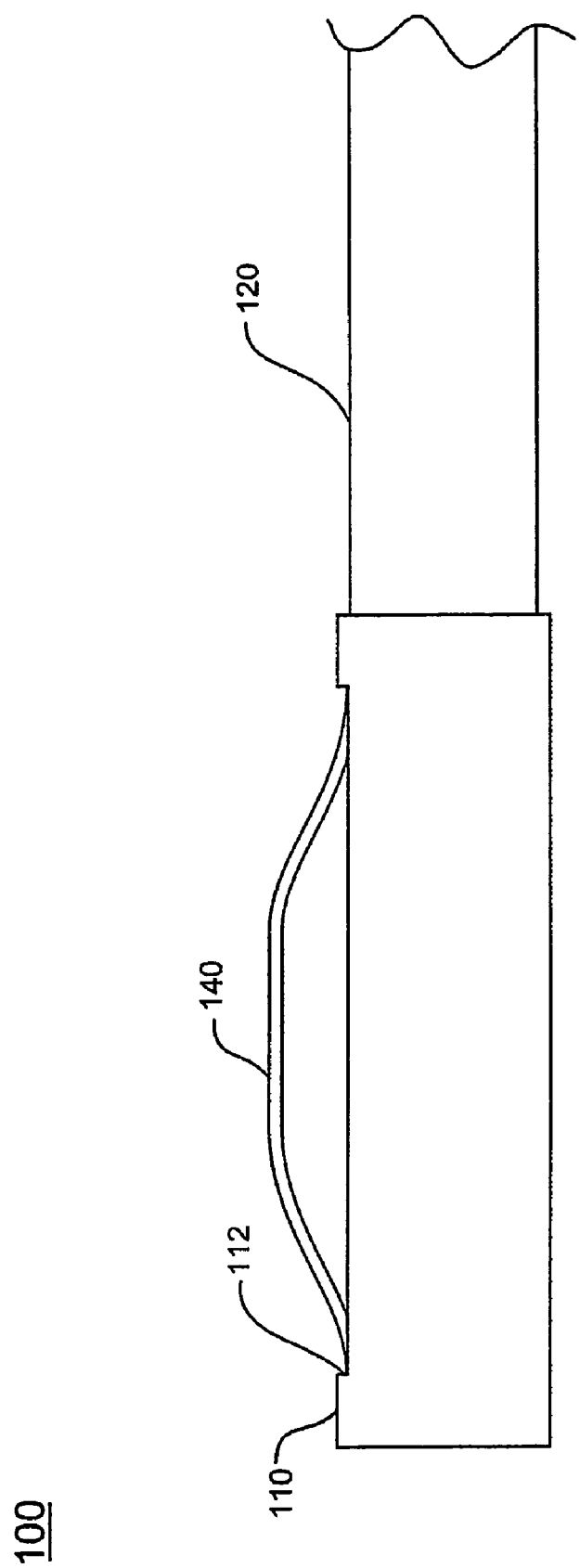
FIG. 4 illustrates a side view of the device illustrated in FIG. 1 in a deployed configuration.

FIG. 3 is a cross-section view of the embodiment illustrated in FIG. 1, taken along line 3-3. As illustrated in FIG. 3, treatment device 100 further includes compression member or spring 140. Spring 140 is in a restrained delivery configuration in FIG. 3, and is restrained by sleeve 110. Spring 140 may comprise any biocompatible material capable of bias. In one embodiment, spring 140 is a flat spring. In another embodiment, spring 140 comprises a pre-shaped member capable of forming a compression configuration when the restraint by sleeve 110 is released, as shown in FIG. 4. Spring 140 may comprise, for example, stainless steel, nitinol, cobalt based alloy, titanium alloy, rigid thermoplastic, thermoset plastic, or a combination thereof. Sleeve 110 Is rotatable about tube 120 and spring 140 to align side port 112 with spring 140. Alternatively, sleeve 110 may be held stationary while tube 120 and spring 140 are rotated there within to align spring 140 with side port 112.

In one embodiment of the invention, treatment device 100 assumes a compression configuration that acts against an interior wall of a coronary sinus to deform the adjacent cardiac valve annulus. FIG. 4 illustrates a side view of the treatment device 100 illustrated in FIGS. 1-3 with spring 140 distending through side port 112 in the compression configuration. To enable spring 140 to distend through side port 112, tube 120 is rotated with respect to sleeve 110.

Those of ordinary skill in the art will readily recognize that the treatment device depicted in FIGS. 1-4 can be readily modified to create different compression configurations. Different compression configurations may be created by varying the length of side port 112, by varying the number of side ports 112, and/or by varying the shape and number of springs 140. Various compression configurations may be provided in a single treatment device 100 by providing a stepped side port with varying widths or radii.

Figure 5:
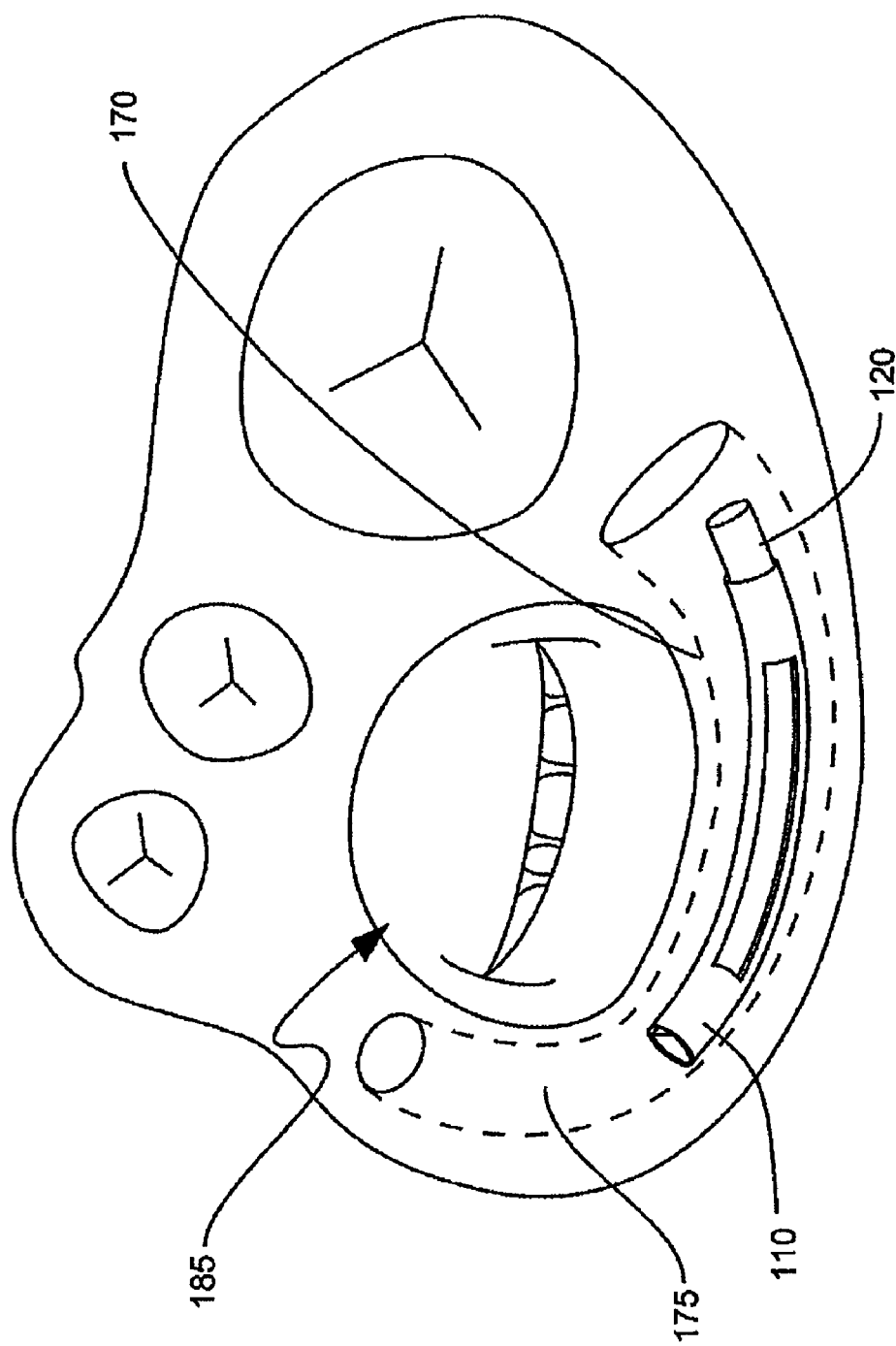
FIG. 5 is an illustration of a device in accordance with the present invention disposed in a coronary sinus prior to deployment adjacent a dilated mitral valve.

FIG. 5 is an illustration of treatment device 100 shown in FIGS. 1-4 in the delivery configuration immediately prior to deployment. Diseased mitral valve 185 is shown incompletely closed, indicating a condition causing mitral valve regurgitation. Coronary sinus 175 lies along the atrioventricular groove on the exterior of the heart proximate mitral valve 185. Treatment device 100 is shown disposed within coronary sinus 175.

Figure 6:
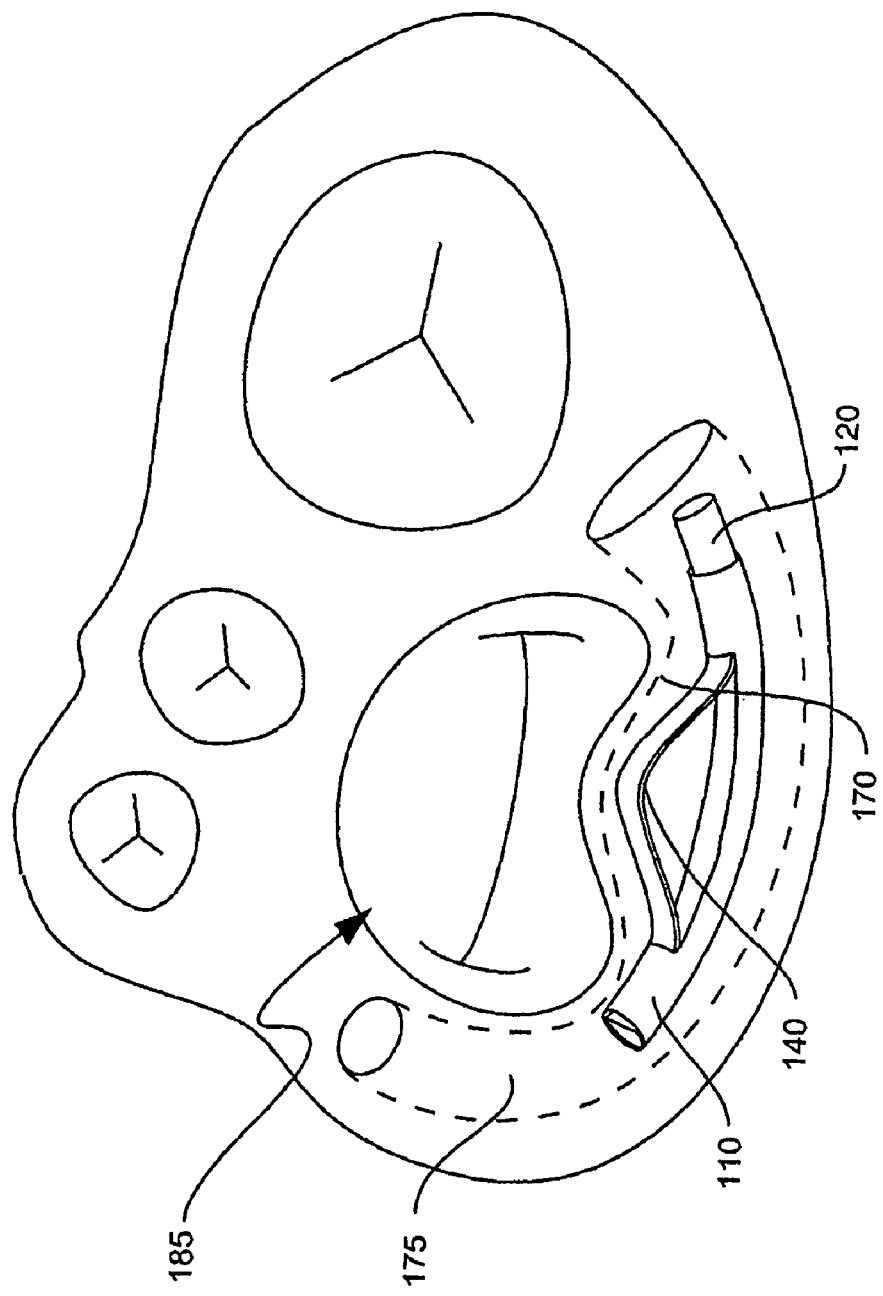
FIG. 6 is an illustration of a device in accordance with the present invention disposed in a coronary sinus after deployment adjacent a mitral valve.

FIG. 6 illustrates treatment device 100, deployed in coronary sinus 175 in a position proximate mitral valve 185. As shown in FIG. 6, the deployed treatment device 100 assumes a compression configuration. After deployment, compression member (spring) 140 extends transversely against a wall of coronary sinus 175 to deform the shape of the coronary sinus and at least a portion of the annulus of mitral valve 185 to allow the valve leaflets to achieve a better seal, and thus reduce mitral valve regurgitation.

FIGS. 5 and 6 also illustrate that treatment device 100 has an outer diameter substantially spanning the inside diameter of the coronary sinus. FIGS. 5 and 6 further illustrate that, when treatment device 100 is implanted, lumen 122 provides a conduit to maintain blood flow through the coronary sinus substantially equal to the amount of blood flow through the coronary sinus without the implant. The close proximity of spring 140 to the coronary sinus wall 170 does not require a great deal of deflection of spring 140 to affect the required change in the mitral valve annulus. Additionally, the close proximity of spring 140 to the wall of the coronary sinus allows the clinician to apply a low level of compression to the wall of the coronary sinus in order to affect a change in the mitral valve annulus sufficient to reduce or eliminate valve regurgitation. This ability to apply a reduced amount of pressure to the wall of the coronary sinus substantially decreases the risk of damaging the wall of the coronary sinus.

It is desirable that treatment device 100 be visible during the implantation procedure. The implantation procedure may be visualized using fluoroscopy, echocardiography, intravascular ultrasound, angioscopy, or another means of visualization to aid in positioning. In one embodiment, the surface of each component of treatment device 100, illustrated in FIGS. 1-6, is treated with a substance to enable visualization of the treatment device throughout the implantation procedure. Accurate imaging of the treatment device can ensure the treatment device is delivered as intended by the clinician. Substances to enable imaging of the system are known to those of ordinary skill in the art.

Treatment device 100 of FIGS. 1-6 may be delivered to the coronary sinus either through surgical access e.g., thoracotomy, port access, or via percutaneous transluminal technique. In one method, the treatment device is delivered transluminally using a catheter based delivery system illustrated in FIG. 7 and described below. Numerous approaches to deliver a catheter to a position within the coronary sinus are known to those of ordinary skill In the art.

Figure 7:
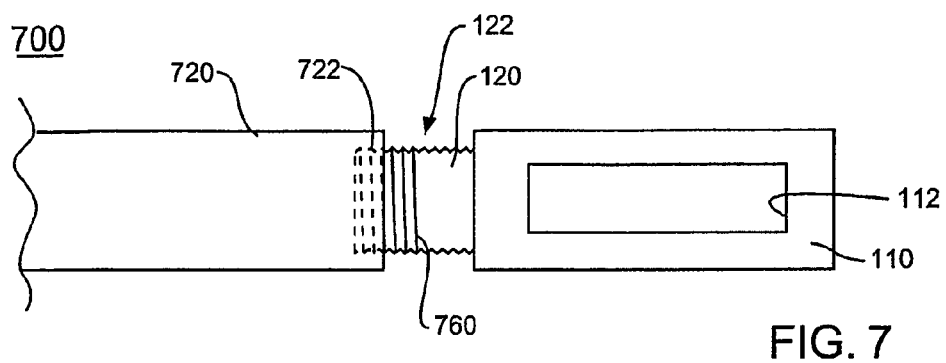
FIG. 7 is a side view of one embodiment of a delivery system in accordance with another aspect of the present invention.

FIG. 7 illustrates one embodiment of delivery system 700 in accordance with the Invention. FIG. 7 uses like reference numbers for like elements illustrated in FIGS. 1-6. The treatment device illustrated in FIGS. 1-6 is delivered to the desired location within the coronary sinus and is to remain deployed at the delivery site after the end of the deployment procedure. FIG. 7 illustrates one embodiment of a delivery system 700 configured to deliver the device of FIGS. 1-6 through the vasculature, deploy the treatment device, and be withdrawn through the vasculature.

FIG. 7 illustrates delivery catheter 720 releasably attached to tube 120 via a release mechanism. Delivery catheter 720 comprises a flexible, biocompatible polymeric material such as polyurethane, polyethylene, nylon, or polytetrafluroethylene (PTFE). FIG. 7 further illustrates side port 112 in sleeve 110. FIG. 7 illustrates male threaded attachment 760 at proximal end 122 of tube 120, and mating female threaded receiver 722 In delivery catheter 720. Alternatively, the attachment and receiver may be reversed, so that threaded attachment 760 is disposed upon delivery catheter 720 and threaded receiver 722 is disposed within tube 120. Threaded receiver 722 and threaded attachment 760 are configured, assembled and tightened such that a predetermined amount of torque is required to release, and begin unscrewing, the connection between the two elements. The predetermined amount of release torque may be higher than the amount of torque required to rotate sleeve 110 to deploy spring 140 through side port 112. Alternatively, sleeve 110 may be rotated in one direction to deploy spring 140 through side port 112, and receiver 722 and attachment 760 may be unscrewed by rotating delivery catheter 720 in the opposite direction such that the relative amounts of torque required for each operation are unimportant.

Those of ordinary skill in the art will readily recognize that delivery catheter 720 must withstand torsional forces and transmit those torsional forces. In one embodiment, delivery catheter 720 comprises a reinforcing structure. In another embodiment, delivery catheter 720 includes a reinforcing structure comprising filamentous braid.

Figure 8:
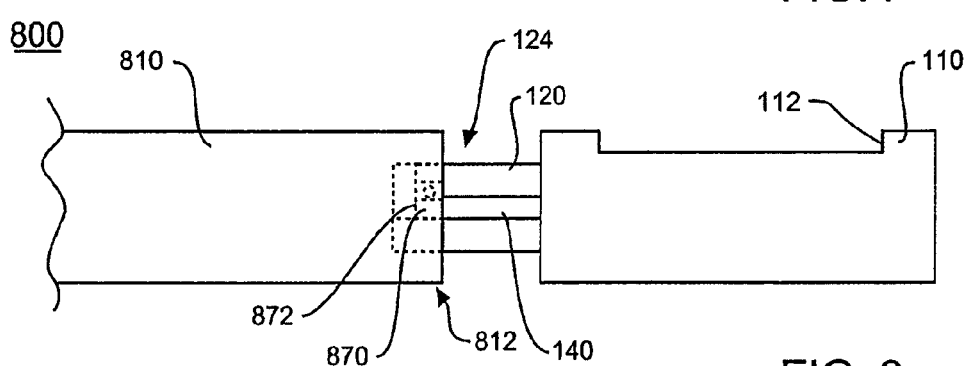
FIGS. 8 and 9 are side views of another embodiment of a delivery device in accordance with the invention.
Figure 9:
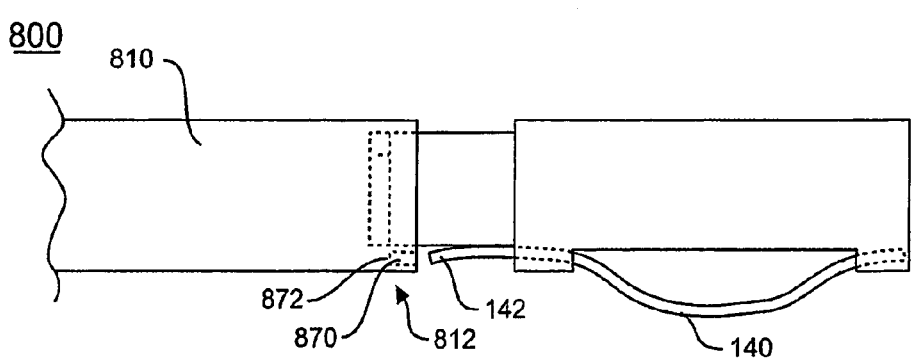

FIGS. 8 and 9 illustrate another embodiment of a delivery system 800 for delivering treatment device 100 illustrated in FIGS. 1-6. FIGS. 8 and 9 illustrate proximal end 124 of tube 120 partially disposed within driving catheter 810 before deployment. Driving catheter 810 is rotatably disposed around proximal end 124 of tube 120. Driving catheter 810 includes keyway 870 at distal end 812 for receiving proximal end 142 of spring 140. Before deployment, proximal end 142 of spring 140 is disposed within keyway 870 effectively locking tube 120 to driving tube 810. Before deployment, spring 140 is in its restrained delivery configuration and proximal end 142 abuts an interior wall 872 of keyway 870.

FIG. 9 illustrates treatment device 100 of FIG. 8 after deployment, wherein proximal end 142 of spring 140 is disengaged from driving catheter 810. As illustrated in FIG. 9, spring 140 has distended through side port 112 to assume its compression configuration. Because spring 140 is in its compression configuration, proximal end 142 of spring 140 has pulled away from interior wall 872 of keyway 870, and proximal end 142 is no longer disposed within keyway 870, thereby releasing driving catheter 810 from tube 120. Driving catheter 810 may be withdrawn, leaving the treatment device deployed in the coronary sinus.

FIG. 10 illustrates an embodiment of a method for treating mitral valve regurgitation using treatment device 100. Method 1000 begins with the delivery of treatment device 100 through the patient's vasculature and into the coronary sinus via delivery system 700 (Block 1010). Treatment device 100 may be delivered by any route suitable for accessing the coronary sinus. In one embodiment, treatment device 100 is carried upon the delivery catheter. Treatment device 100 is delivered as shown in FIG. 1, with compression member 140 restrained within sleeve 110 due to the non-aligned between compression member 140 and side port 112.

Compression member 140 is positioned along the wall of the coronary sinus adjacent to and oriented towards the mitral valve annulus (Block 1020). Next, sleeve 110 is rotated about tube 120 to align side port 112 with the pre-positioned compression member 140 (Block 1030). In one embodiment, compression member 140 is a flat spring. In another embodiment, compression member 140 comprises a pre-shaped material restrained from assuming the compression configuration by surrounding sleeve 110 and the non-alignment of compression member 140 and side port 112.

In an alternative method, side port 112 may be positioned along the wall of the coronary sinus adjacent to and oriented towards the mitral valve annulus. Then, tube 120 and compression member 140 are rotated within sleeve 110 to align compression member 140 with side port 112.

Compression member 140 deploys through side port 112 of sleeve 110 responsive to the alignment of side port 112 with compression member 140. Deployed compression member 140 extends transversely against a wall of coronary sinus 175 to deform the shape of the coronary sinus and at least a portion of the annulus of mitral valve 185, causing the valve leaflets to achieve a better seal, and thus reduce mitral valve regurgitation.

Other embodiments of treatment device 100 may include additional features depending upon the desired clinical performance. For example, treatment device 100 may be provided with heparin or other antithrombogenic agents. In another or the same embodiment treatment, device 100 may include elastomers such as silicone, neoprene, latex or others to soften the surface and reduce the risk of trauma to the coronary sinus wall.

Variations and alterations in the design, manufacture and use of the treatment device, system and method are apparent to one skilled in the art, and may be made without departing from the spirit and scope of the present invention. While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A system for treating cardiac valve regurgitation, the system comprising:
   a device for treating cardiac valve regurgitation comprising:
   a tube including a lumen there through;
   a compression member carried on the tube; and
   a sleeve rotatably disposed about the tube and the compression member, the sleeve including a side port formed therein, wherein the side port is alignable with the compression member by relative rotation between the sleeve and the compression member;
   a delivery catheter; and
   a release mechanism to releasably attach the delivery catheter to a treatment device,
   wherein the release mechanism comprises:

a threaded attachment portion at a proximal end of the tube for threaded attachment to a threaded receiver portion disposed at a distal end of the delivery catheter.

2. A system for treating cardiac valve regurgitation, the system comprising:
a device for treating cardiac valve regurgitation comprising:
a tube including a lumen there through;
a compression member carried on the tube; and
a sleeve rotatably disposed about the tube and the compression member, the sleeve including a side port formed therein, wherein the side port is alignable with the compression member by relative rotation between the sleeve and the compression member;
a delivery catheter; and
a release mechanism to releasably attach the delivery catheter to a treatment device,
wherein the delivery catheter comprises a driving catheter, the driving catheter including a keyway disposed at a distal end, the keyway being sized and shaped for receiving a proximal end of the compression member when the compression member is in a delivery configuration.

3. A method for treating cardiac valve regurgitation, the method comprising:
providing a treatment device comprising a compression member disposed exteriorly on a tube and a sleeve rotatably disposed about the tube and the compression member;
positioning the treatment device in a blood vessel adjacent a cardiac valve; and
effectuating relative rotation between the sleeve and the compression member to align the compression member with a side port in the sleeve, thus deploying the compression member through the side port and into contact with the blood vessel.

4. The method of claim 3 wherein deploying the compression member deforms the blood vessel and applies a compressive force to the cardiac valve.

5. The method of claim 3 wherein the blood vessel adjacent the cardiac valve is a coronary sinus.

6. The method of claim 3 wherein positioning the treatment device in a blood vessel is executed via a delivery catheter.

7. The method of claim 6 further comprising:
releasing the treatment device from the delivery catheter after the compression member has been deployed.

8. The method of claim 7 wherein releasing the treatment device from the delivery catheter comprises rotating the delivery catheter in relation to the treatment device to unscrew a threaded engagement there between.

9. The method of claim 3 wherein deploying the compression member through the side port transforms the compression member from a delivery configuration to a compression configuration.

* * * * *